United States Patent
Chu

(10) Patent No.: US 9,408,621 B2
(45) Date of Patent: Aug. 9, 2016

(54) MEDICAL RETRIEVAL DEVICES AND RELATED METHODS OF USE

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 134 days.

(21) Appl. No.: 14/294,346

(22) Filed: Jun. 3, 2014

(65) Prior Publication Data

US 2015/0066049 A1 Mar. 5, 2015

Related U.S. Application Data

(60) Provisional application No. 61/872,196, filed on Aug. 30, 2013.

(51) Int. Cl.
*A61B 17/22* (2006.01)
*A61B 17/221* (2006.01)

(52) U.S. Cl.
CPC ....... *A61B 17/221* (2013.01); *A61B 2017/2215* (2013.01)

(58) Field of Classification Search
CPC ............... A61B 17/221; A61B 2017/2215; A61B 2017/2212; A61B 2017/22034; A61B 2017/22035; A61B 17/22031; A61B 1/00085; A61F 2002/016; A61F 2002/018; A61F 2/01; A61F 2/013; A61F 2230/0091; A61F 2230/0093; A61F 2230/0086; A61F 2230/0089
USPC .................................. 606/200, 127
See application file for complete search history.

(56) References Cited

U.S. PATENT DOCUMENTS

| 5,152,777 | A | * | 10/1992 | Goldberg | A61F 2/01 606/200 |
| 5,387,219 | A | * | 2/1995 | Rappe | A61B 17/1214 606/1 |
| 5,527,326 | A | * | 6/1996 | Hermann | A61B 17/221 606/159 |
| 5,667,525 | A | * | 9/1997 | Ishibashi | A61B 17/221 606/206 |
| 5,906,622 | A | | 5/1999 | Lippitt et al. | |
| 5,924,175 | A | | 7/1999 | Lippitt et al. | |
| 6,159,220 | A | * | 12/2000 | Gobron | A61B 17/221 606/127 |
| 6,383,195 | B1 | * | 5/2002 | Richard | A61B 17/221 606/114 |
| 7,041,108 | B2 | | 5/2006 | Lippitt et al. | |
| 7,210,210 | B2 | | 5/2007 | Lippitt et al. | |
| 7,322,989 | B2 | * | 1/2008 | Teague | A61B 17/221 606/114 |
| 2006/0052797 | A1 | * | 3/2006 | Kanamaru | A61B 17/22 606/113 |
| 2006/0293697 | A1 | * | 12/2006 | Nakao | A61B 17/221 606/127 |

(Continued)

FOREIGN PATENT DOCUMENTS

WO WO 0145590 A2 * 6/2001 ............. A61F 2/013

*Primary Examiner* — Katrina Stransky

(74) *Attorney, Agent, or Firm* — Bookoff McAndrews, PLLC

(57) ABSTRACT

A medical device that may include a plurality of branch members forming a basket movable between a collapsed configuration and an expanded configuration is disclosed. Each branch member may include a proximal coil, and a distal coil. Each branch member may also include an uncoiled portion disposed between the proximal coil and the distal coil, and a movable portion.

19 Claims, 4 Drawing Sheets

(56) References Cited

U.S. PATENT DOCUMENTS

| | | | |
|---|---|---|---|
| 2007/0027456 A1* | 2/2007 | Gartner | A61B 17/0057 606/113 |
| 2007/0118165 A1* | 5/2007 | DeMello | A61B 17/221 606/159 |
| 2008/0269774 A1* | 10/2008 | Garcia | A61B 17/221 606/127 |
| 2010/0016875 A1* | 1/2010 | Nakao | A61B 17/221 606/159 |
| 2012/0004666 A1* | 1/2012 | Cowley | A61B 17/221 606/127 |
| 2014/0142610 A1* | 5/2014 | Larsen | A61B 17/12172 606/200 |

* cited by examiner

MEDICAL RETRIEVAL DEVICES AND RELATED METHODS OF USE

CROSS-REFERENCE TO RELATED APPLICATION

This application claims the benefit of U.S. Provisional Application No. 61/872,196, filed Aug. 30, 2013, the disclosure of which is incorporated herein by reference in its entirety.

TECHNICAL FIELD

Various embodiments of the present disclosure relate generally to medical retrieval devices and related systems and methods. More specifically, the present disclosure relates to devices, systems, and methods for retrieving objects within a patient.

BACKGROUND

Medical retrieval devices are often utilized for removing organic material (e.g., blood clots, tissue, and biological concretions such as urinary, biliary, and pancreatic stones) and inorganic material (e.g., components of a medical device or other foreign matter), which may obstruct or otherwise be present within a patient's body cavities. For example, concretions can develop in certain parts of the body, such as in the kidneys, pancreas, and gallbladder. Minimally invasive medical procedures are used to remove these concretions through natural orifices, or through an incision, such as during a percutaneous nephrolithotomy (PNCL) procedure. Further, lithotripsy and ureteroscopy, for example, are used to treat urinary calculi (e.g., kidney stones) in the ureter of a patient.

Further, known medical retrieval devices are complex, requiring many components and labor-intensive manufacturing processes. The assembly of small parts often requires visual magnification and specialized training. The available joining mechanisms often increase the profile of the medical retrieval devices beyond optimal design parameters, and are often the weakest structural points. These drawbacks result in medical retrieval devices that are bulky, expensive, and prone to failure.

Thus, there remains a need for improved medical retrieval devices having reduced profiles and fewer components.

SUMMARY OF THE DISCLOSURE

The present disclosure includes medical retrieval devices and related methods of use.

In accordance with an embodiment, the present disclosure is directed to a medical device having a plurality of branch members forming a basket movable between a collapsed configuration and an expanded configuration. Each branch member may include a proximal coil, and a distal coil. Each branch member may also include an uncoiled portion disposed between the proximal coil and the distal coil, and a movable portion.

Various embodiments of the disclosure may include one or more of the following aspects: each of the plurality of branch members being formed from two separate filaments; wherein a first branch member of the plurality of branch members is formed such that the proximal coil and distal coil are formed from a first filament and the movable portion is formed from a second filament; wherein the movable portion of the second filament is disposed through the distal coil and the proximal coil of the first filament; wherein a second branch member of the plurality of branch members is formed by a movable portion of the first filament, and a proximal coil and distal coil of a third filament; wherein the plurality of branch members are formed by an equal number of filaments; further including a sheath coupled to each of the plurality of branch members proximal to the plurality of proximal coils; wherein each of the plurality of movable portions extend proximally through the sheath; wherein the basket is configured to: move from the expanded configuration to the collapsed configuration by a proximal movement of each of the movable portions, and move from the collapsed configuration to the expanded configuration by a distal movement of each of the movable portions; wherein each branch member further includes an uncoiled portion between the proximal coil and the sheath; wherein each of the plurality of proximal coils is directly coupled to the sheath; wherein each movable portion includes a bridge portion extending distally from a respective distal coil toward an adjacent branch member; and wherein each bridge portion has a shorter length in the collapsed configuration than in the expanded configuration.

In accordance with an embodiment, the present disclosure is directed to a medical device having a plurality of branch members forming a basket having a movable between a collapsed configuration and an expanded configuration. The basket may include a first plurality of coils disposed on the plurality of branch members, and each of the first plurality of coils may be staggered about a longitudinal axis of the medical device from a remaining plurality of first coils. The basket may also include a second plurality of coils disposed on the plurality of branch members, and each of the second plurality of coils may be staggered about the longitudinal axis of the medical device from a remaining plurality of second coils.

Various embodiments of the disclosure may include one or more of the following aspects: wherein each of the first plurality of coils are disposed on one of the plurality of branch members with a corresponding coil of the second plurality of coils; wherein each of the plurality of branch members are substantially parallel to the longitudinal axis of the medical device when the basket is in the collapsed configuration; and wherein each of the plurality of branch members extends radially outward about the longitudinal axis of the medical device when the basket is in the expanded configuration.

In accordance with an embodiment, the present disclosure is directed to a medical device having a plurality of branch members forming a basket movable between a collapsed configuration and an expanded configuration. Each branch member may include a proximal coil, a distal coil, an uncoiled portion disposed between the proximal coil and the distal coil, and a movable portion. Each of the plurality of distal coils may be staggered about a longitudinal axis of the medical device from a remaining plurality of distal coils; and each of the plurality of proximal coils may staggered about the longitudinal axis of the medical device from a remaining plurality of proximal coils.

Various embodiments of the disclosure may include one or more of the following aspects: wherein each uncoiled portion is located at approximately a midpoint between a respective distal coil and proximal coil; and wherein the plurality of annularly arranged branch members are formed by an equal number of filaments.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts.

Figure 1:
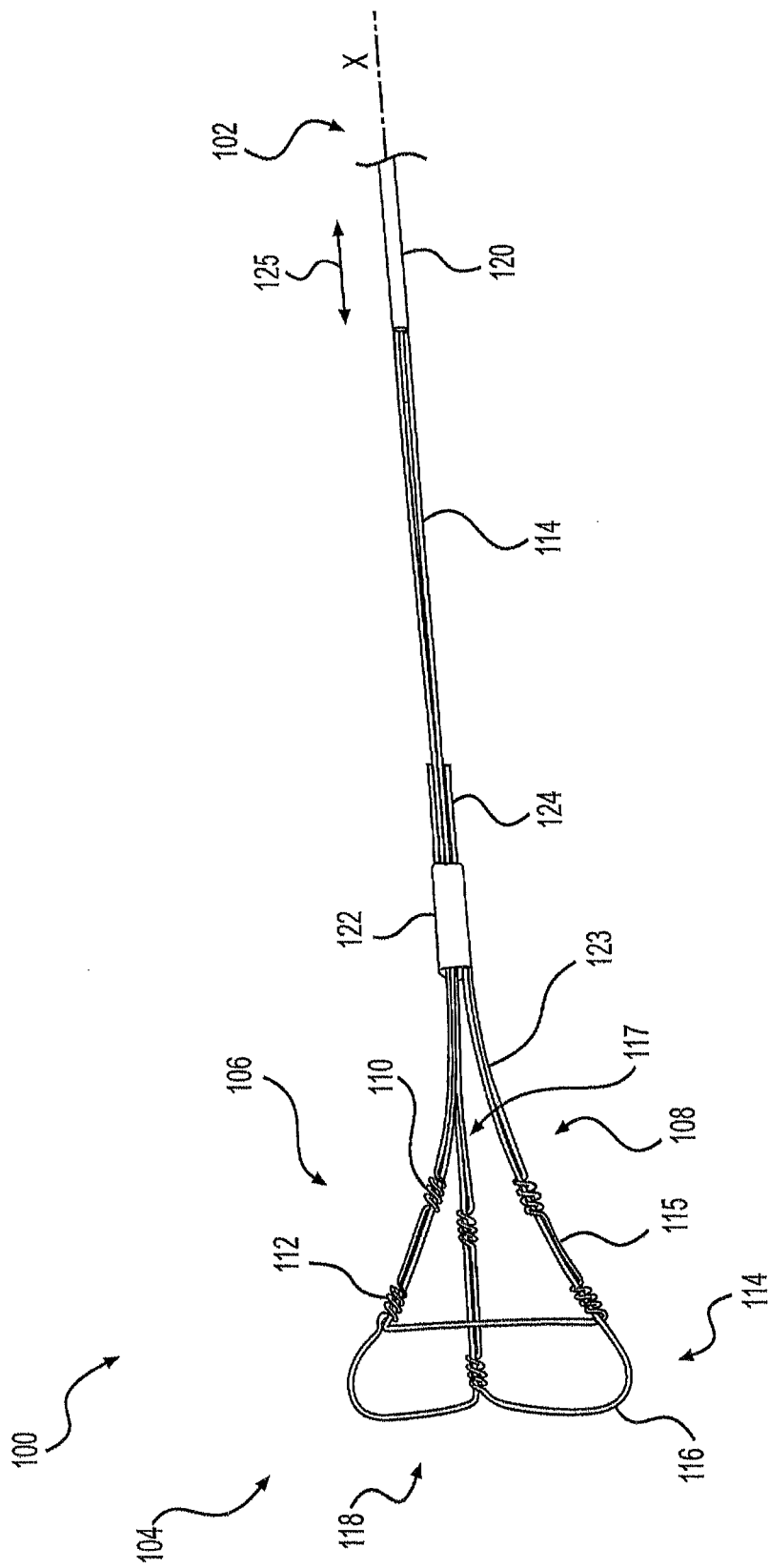
FIG. 1 is a partial side perspective view illustration of a medical retrieval device in an expanded configuration in accordance with an embodiment of the present disclosure.

As shown in FIG. 1, a medical device 100 according to an exemplary embodiment of the present disclosure may extend from a proximal end 102 toward a distal end 104. Medical device 100 may include a basket 106 disposed at distal end 104, and may be configured to reciprocally move between a collapsed configuration and an expanded configuration. In the embodiment shown in FIG. 1, basket 106 is in the expanded configuration. In the expanded configuration, a plurality of branch members 108 may be disposed radially outward about a longitudinal axis X of medical device 100. The plurality of branch members 108 may be spaced apart from one another in a substantially uniform distribution. For example, in the embodiment shown in FIG. 1, medical device 100 may include three branch members 108 that are spaced about 120° from one another. In an alternative embodiment (not shown) having four branch members 108, each branch member 108 may be disposed about 90° from an adjacent branch member 108. However, it should be noted that any other suitable number of branch members may alternatively be utilized, if desired.

Each branch member 108 may include a proximal coil 110, a distal coil 112, and a movable portion 114 that extends through both distal coil 112 and proximal coil 110. A gap 115 (i.e., an uncoiled portion) may be disposed between proximal coil 110 and distal coil 112. Movable portion 114 may include a bridge portion 116 that is distal to distal coil 112 when medical device 100 is in the expanded configuration. In the expanded configuration, a user may manipulate medical device 100 to capture materials within a patient, such as, e.g., a kidney stone or the like. Materials may enter basket 106 via a side opening 117 defined by adjacent branch members 108, or via a distal opening 118 defined by the plurality of bridge portions 116. Proximal and distal coils 110, 112 may have any suitable number of revolutions and have any suitable cross-sectional profile, such as, e.g., a circular or rectangular cross-sectional profiles. Proximal and distal coils 110, 112 may be wound in either a clockwise or counterclockwise direction. In some embodiments, proximal coils 110 may have the same pitch and geometry as distal coils 112, while in other embodiments, proximal coils 110 may have a different pitch and/or geometry than distal coils 112.

In some embodiments, the plurality of branch members 108 may have a bias such that in an assembled configuration, the plurality of branch members 108 are naturally urged radially outward from longitudinal axis X. In an alternative embodiment, each of the plurality of branch members may be pre-bent radially outward of longitudinal axis X at bridge portion 116. Alternatively, each of the plurality of branch members 108 may have another suitable shape, such as, e.g., a curve inwards toward longitudinal axis X to aid with object retrieval.

Movable portion 114 may extend proximally through distal coil 112 and proximal coil 110 toward proximal end 102. A proximal end of movable portion 114 may be coupled to an actuation member 120. Actuation member 120 may be a filament, braided wire, rope, rod, or other suitable actuation member that may be coupled to an actuator (not shown). In an alternative embodiment, the plurality of movable portions 114 may be coupled to the actuator directly. The actuator may be disposed within a housing, e.g., a handle, and may encompass any suitable actuator configured to reciprocally move actuation member 120 and/or movable portion(s) 114 in a longitudinal direction including, but not limited to, sliding mechanisms, rotating mechanisms, pushing mechanisms, or the like. A sheath 122 may be disposed distal to actuation member 120, proximal to proximal coil 110, and may be coupled to the plurality of branch members 108. A gap 123 (i.e., an uncoiled portion) may be disposed between proximal coil 110 and sheath 122. In the embodiment shown in FIG. 1, proximal coil 110 may be disposed approximately at a mid-point between distal coil 112 and sheath 122. In an alternative embodiment, proximal coil may instead be disposed closer to either distal coil 112 or sheath 122.

In some embodiments, a fixed end 124 of each branch member 108 may be fixed to sheath 122, while other portions of each branch member 108, e.g., movable portion 114, may be configured to move relative to sheath 122. Fixed end 124 may be fixed to sheath 122 by any suitable mechanism including, but not limited to, adhesives, friction fits, crimping, or the like. Sheath 122 may remain in a fixed longitudinal position while actuation member 120 is directed proximally by the actuator to move medical device 100 between the collapsed and expanded configurations. In other embodiments, sheath 122 may be directed distally while actuation member 120 is concurrently directed proximally by the actuator to move medical device 100 between the collapsed and expanded configurations. Thus, movable portion 114 may move along path 125 that travels substantially along longitudinal axis X.

Figure 2:
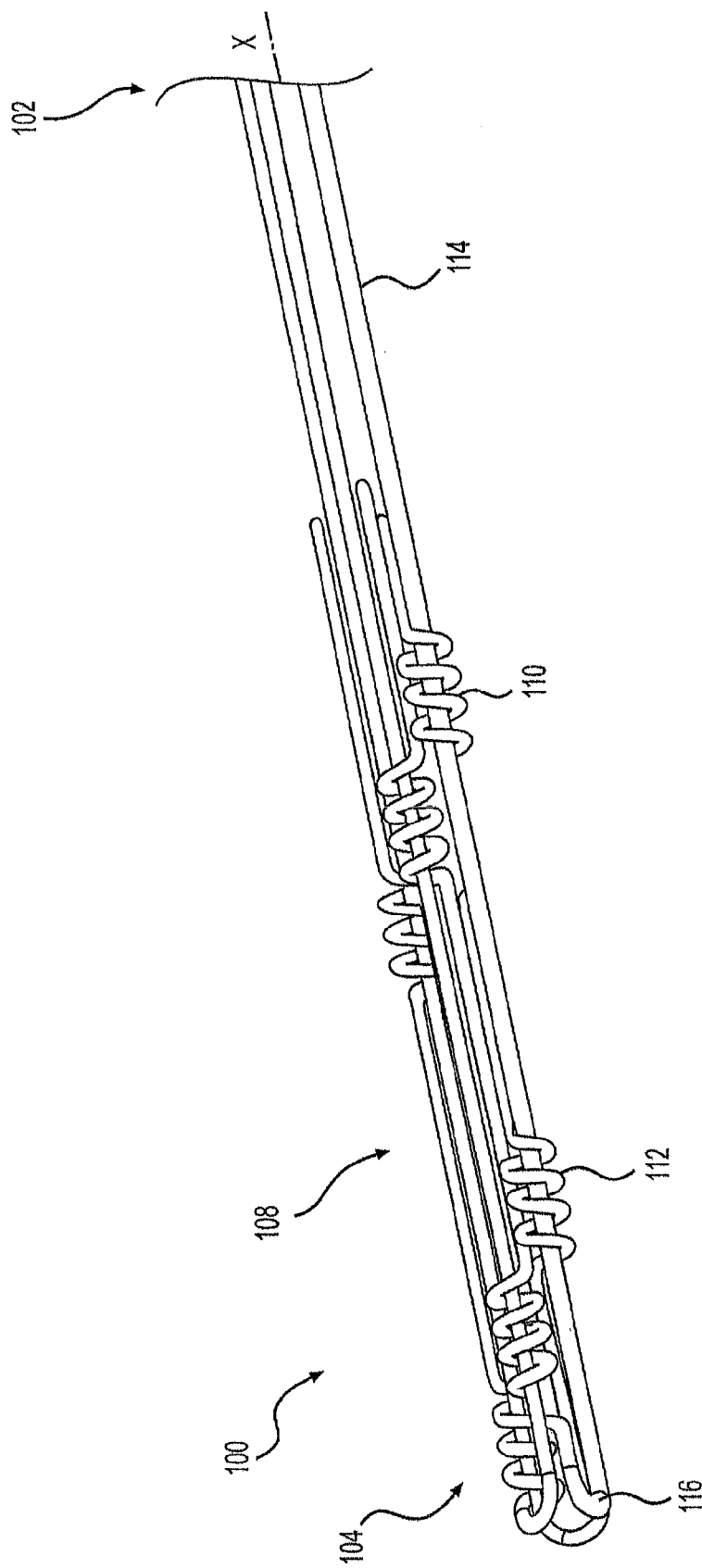
FIG. 2 is a partial side perspective view illustration of the medical retrieval device of FIG. 1 in a collapsed configuration.

In FIG. 2, medical device 100 is shown in the collapsed configuration. In the collapsed configuration, each branch member 108 may be substantially parallel to longitudinal axis X. That is, each branch member 108 may be directed radially inward toward longitudinal axis X from the expanded position as a result of the proximal retraction of actuation member 120 (shown only in FIG. 1) and/or movable portions 114. In the collapsed configuration, bridge portions 116 may be shorter than in the expanded configuration of medical device 100. Additionally, side openings 117 and distal opening 118 (referring to FIG. 1) may not be disposed in the collapsed configuration.

As best seen in FIG. 2, each proximal coil 110 may be longitudinally staggered with respect to a remaining plurality of proximal coils 110 such that in the collapsed configuration, each proximal coil 110 is located at a different position along longitudinal axis X. Similarly, each distal coil 112 may be longitudinally staggered with respect to a remaining plurality of distal coils 112 such that in the collapsed configuration, each distal coil 112 is located at a different position along longitudinal axis X. In one embodiment, a proximal coil 110 (or a distal coil 112) is staggered from a remaining plurality of proximal coils 110 (or distal coils 112) such that the proximal coils 110 do not exhibit any overlap when in the collapsed configuration. Such an arrangement may significantly reduce the profile of medical device 100. Thus, in the expanded configuration (referring to FIG. 1), each proximal coil 110 and distal coil 112 may have a unique longitudinal position (i.e., may be disposed at a different longitudinal position than each other proximal coil 110 and/or distal coil 112).

In one embodiment, proximal coils 110 may, in the collapsed configuration, generally be configured from end to end such that the plurality of proximal coils 110 form one continuous coil portion extending transversely to longitudinal axis X. Similarly, distal coils 112 may, in the collapsed configuration, generally be configured from end to end such that the plurality of distal coils 112 form one continuous coil portion extending transversely to longitudinal axis X. In an alternative embodiment, proximal coils 110 (or distal coils 112) may partially or fully overlap with each other in the collapsed configuration.

Figure 3:
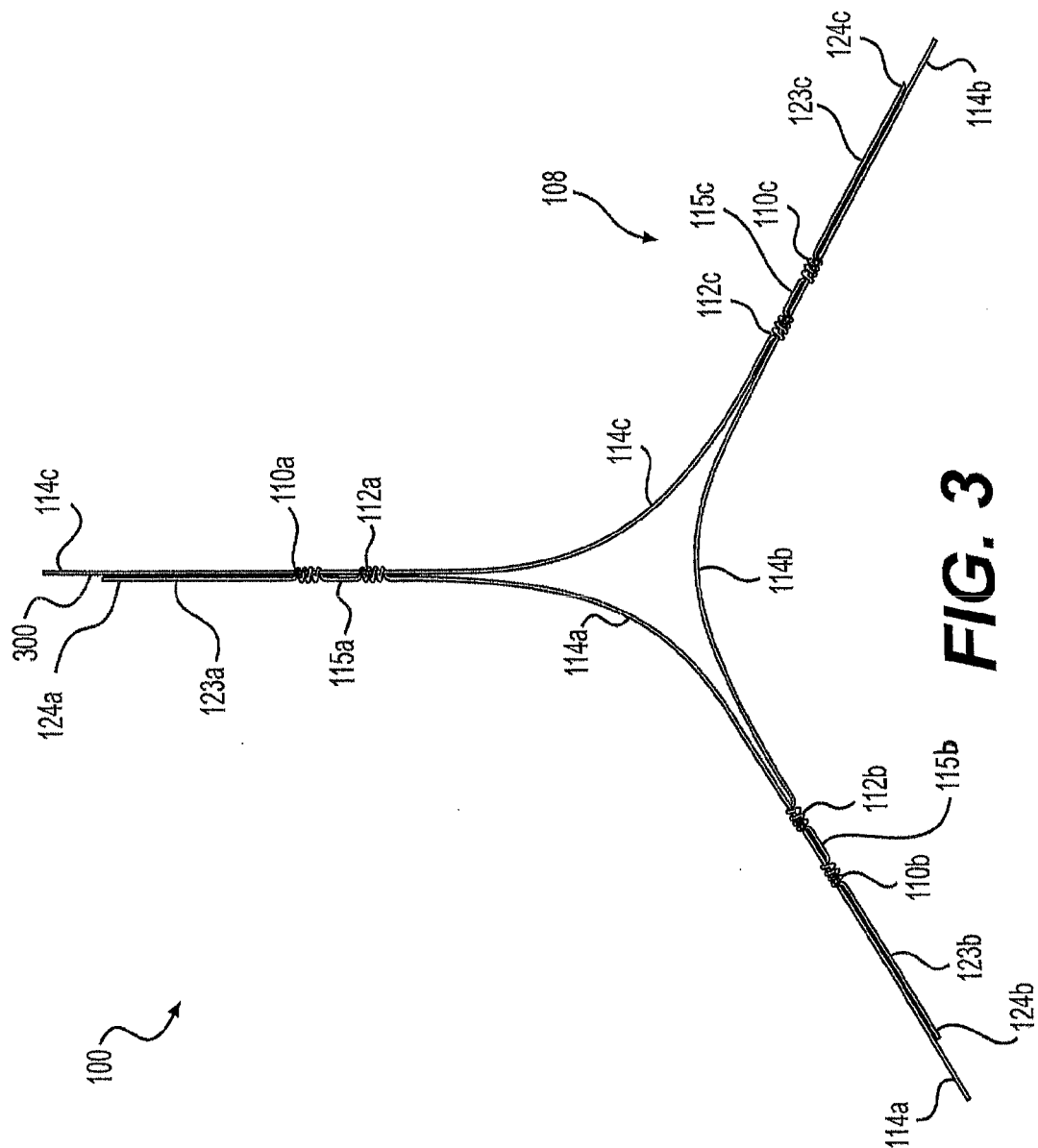
FIG. 3 is a top view illustration of portions of the medical retrieval device of FIG. 1 in a partially-assembled configuration.

Referring to FIG. 3, medical device 100 may be formed from a plurality of continuous filaments 300. In one embodiment, medical device 100 may include three filaments—300a, 300b, and 300c. Filaments 300 may be formed of any suitable material including, but not limited to, metals, polymers, or a combination of materials. In one embodiment, filament 300 may include a metal wire coated with a polymer. In an alternative embodiment, filament 300 may be formed from two or more metals that are co-drawn together. Filament 300 may have any suitable cross-sectional profile such as, e.g., circular, rectangular, ovular, or polygonal. In some embodiments, portions of filament 300 may be flattened, machined, extruded, drawn, or etched into a different profile than a remaining portion of filament 300.

Each filament 300a, 300b, or 300c may include a respective movable portion 114, a distal coil 112, a proximal coil 110, a gap 115, and a fixed end 124. It should be noted that in FIG. 3, each respective movable portion 114, distal coil 112, proximal coil 110, gap 115, and fixed end 124 is designated with the appropriate letter designation a, b, or c. While in the embodiment shown, each filament 300 includes two coils, a proximal coil 110 and a distal coil 112, alternative embodiments may include fewer or additional numbers of coils. A movable portion 114a of a given filament 300a may be directed, e.g., through distal coil 112b and proximal coil 110b of a counterclockwise adjacent filament 300b to form a branch member 108. Further, the movable portion 114c of a clockwise adjacent filament 300c may be directed through the proximal coil 112a and distal coil 110a of the given filament 300a to form another branch member 108. Each of the filaments 300 may be similarly arranged so that the resulting number of branch members 108 may correspond (i.e., is equal) to the number of filaments 300 in a given medical device 100. Thus, each branch member 108 may be formed by two different filaments 300, e.g., the proximal coil 110 and distal coil 112 of first filament 300, and the movable portion 114 of a second filament 300. The portion of each filament 300 that forms distal coil 112 and proximal coil 110 may have a smaller diameter or a lower profile (e.g., flattened), as compared to a remaining portion of each filament 300. The smaller diameter and/or lower profile may reduce an overall profile of medical device 100. Each filament 300 may be friction coated or have another suitable coating to assist with object retrieval and grip.

Figure 4:
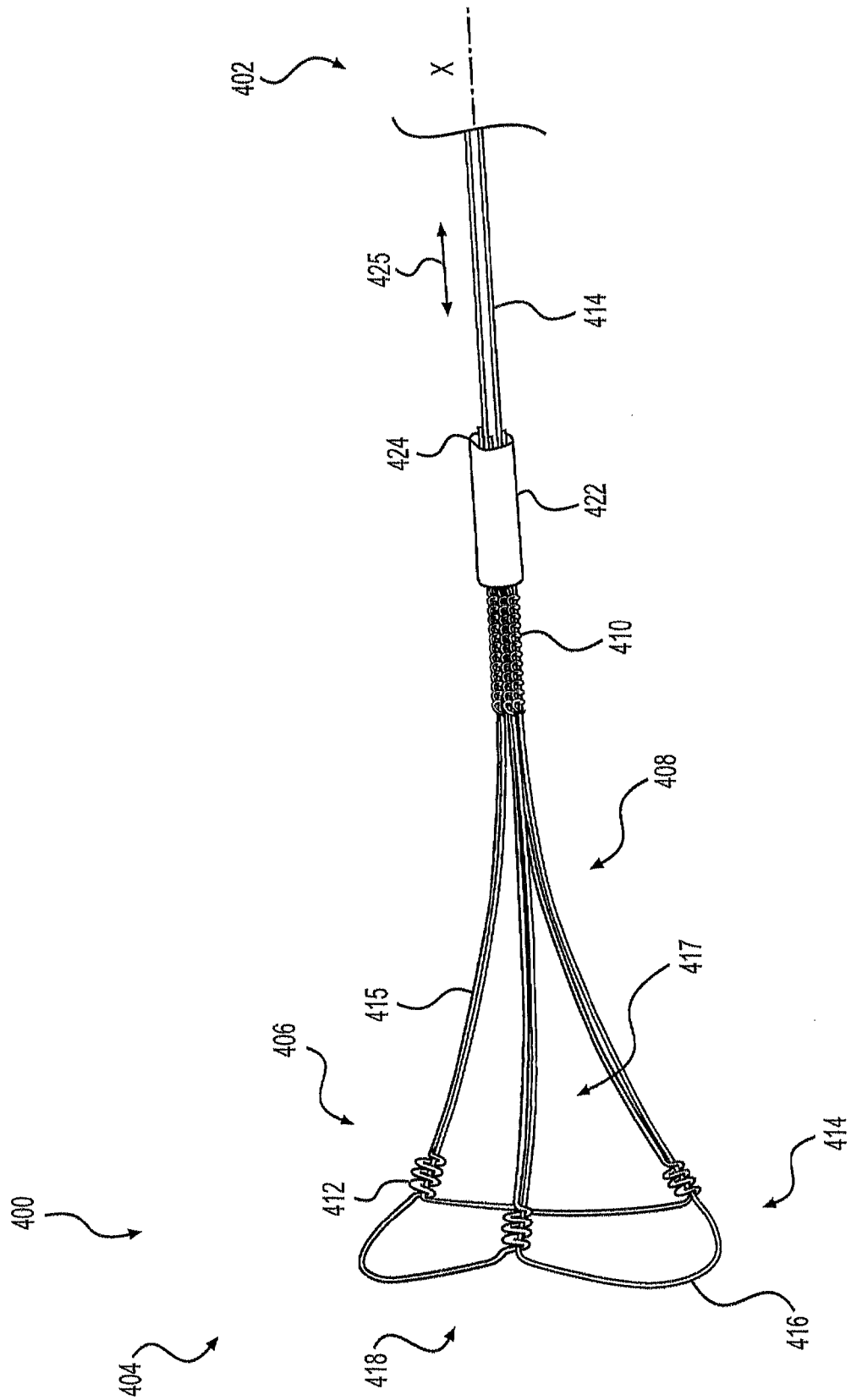
FIG. 4 is a partial side perspective view illustration of a medical retrieval device in an expanded configuration in accordance with an embodiment of the present disclosure.

As shown in FIG. 4, a medical device 400 according to an exemplary embodiment of the present disclosure may extend from a proximal end 402 toward a distal end 404. Medical device 400 may include a basket 406 disposed at distal end 404, and may be configured to reciprocally move between a collapsed configuration and an expanded configuration. In the embodiment shown in FIG. 4, basket 406 is in the expanded configuration. In the expanded configuration, a plurality of branch members 408 may be disposed radially outward about a longitudinal axis X of medical device 400. The plurality of branch members 408 may be spaced apart from one another in a substantially uniform distribution as described above with reference to branch members 108 of FIG. 1. Thus, in the expanded configuration, each distal coil 412 may have a unique longitudinal position (i.e., may be disposed at a different longitudinal position than each other distal coil 412).

Each branch member 408 may include a proximal coil 410, a distal coil 412, and a movable portion 414 that extends through both distal coil 412 and proximal coil 410. A gap 415 (i.e., an uncoiled portion) may be disposed between proximal coil 410 and distal coil 412. Movable portion 414 may include a bridge portion 416 that is distal to distal coil 412 when medical device 400 is in the expanded configuration. In the expanded configuration, a user may manipulate medical device 400 to capture materials within a patient, such as, e.g., a kidney stone or the like. Materials may enter basket 406 via a side opening 417 defined by adjacent branch members 408, or via a distal opening 418 defined by the plurality of bridge portions 416. In the embodiment shown in FIG. 4, proximal coils 410 may be longer than distal coils 412. However, it should be noted that proximal and distal coils 410, 412 may have other suitable lengths and arrangements similar to proximal and distal coils 110, 112 described with reference to FIGS. 1-3. In some embodiments, distal coils 412 may be staggered in a manner similar to distal coils 112, described above with reference to FIG. 2.

In some embodiments, the plurality of branch members 408 may have a bias such that in an assembled configuration, the plurality of branch members 408 are naturally urged radially outward from longitudinal axis X. In an alternative embodiment, each of the plurality of branch members may be pre-bent radially outward of longitudinal axis X at bridge portion 416. Alternatively, each of the plurality of branch members 408 may have another suitable shape, such as, e.g., a curve inwards toward longitudinal axis X to aid with object retrieval.

Movable portion 414 may extend proximally through distal coil 412 and proximal coil 410 toward proximal end 402. A proximal end of movable portion 414 may be coupled to an actuation member (not shown) and an actuator (not shown). In an alternative embodiment, the plurality of movable portions 414 may be coupled to the actuator directly. A sheath 422 may be disposed proximal to proximal coils 410. In the embodiment shown in FIG. 4, proximal coils 410 may be directly coupled to sheath 422 such that there is no intervening gap or uncoiled portion between proximal coils 410 and sheath 422.

In some embodiments, a fixed end 424 extending proximally from proximal coils 410 may be fixed to sheath 422, movable portion 414 may be configured to move relative to sheath 422. Fixed end 424 may be fixed to sheath 422 by any suitable mechanism including, but not limited to, adhesives, friction fits, crimping, or the like. Sheath 422 may remain in a fixed longitudinal position while movable portions 414 are directed proximally by the actuator to move medical device 400 between the collapsed and expanded configurations. Thus, movable portion 414 may move along path 425 that travels substantially along longitudinal axis X.

The disclosed medical devices may be utilized in any suitable application requiring the capture and removal of materials from the body. The disclosed medical devices may be simple and inexpensive to manufacture, and have improved durability as they may have fewer components prone to failure. The staggering of proximal and distal coils 110, 112 may increase utility of the disclosed medical devices, as they may be suitable for applications requiring reduced-profile baskets. Further, the geometry of the coils may improve basket effectiveness by improving grip. That is, the edges of the coils may act as teeth and increase a gripping surface area, enabling the disclosed medical devices to more securely grasp materials within the body.

Any aspect set forth in any embodiment may be used with any other embodiment set forth herein. Every device and apparatus set forth herein may be used in any suitable medical procedure, may be advanced through any suitable body lumen and body cavity, and may be used to remove material from any suitable body portion. For example, the apparatuses and methods described herein may be used through any natural body lumen or tract, including those accessed orally, vaginally, rectally, nasally, urethrally, or through incisions in any suitable tissue.

It will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only. The following disclosure identifies some other exemplary embodiments.

I claim:

1. A medical device, comprising:
a plurality of branch members forming a basket movable between a collapsed configuration and an expanded configuration, each branch member having:
a proximal coil defining a lumen;
a distal coil defining a lumen;
an uncoiled portion disposed between the proximal coil and the distal coil; and
a movable portion that slides through the lumen of the proximal coil and the lumen of the distal coil to move the basket between the collapsed configuration and the expanded configuration.

2. The medical device of claim 1, each of the plurality of branch members being formed from two separate filaments.

3. The medical device of claim 2, wherein a first branch member of the plurality of branch members is formed such that the proximal coil and distal coil of the first branch member are formed from a first filament and the movable portion of the first branch member is formed from a second filament.

4. The medical device of claim 3, wherein a second branch member of the plurality of branch members includes a movable portion formed by a portion of the first filament, and a proximal coil and distal coil formed by a third filament.

5. The medical device of claim 1, wherein the plurality of branch members are formed by an equal number of filaments.

6. The medical device of claim 1, further including a sheath coupled to each of the plurality of branch members proximal to the plurality of proximal coils.

7. The medical device of claim 6, wherein each of the plurality of movable portions extend proximally through the sheath.

8. The medical device of claim 7, wherein the basket is configured to:
move from the expanded configuration to the collapsed configuration by a proximal movement of each of the movable portions; and
move from the collapsed configuration to the expanded configuration by a distal movement of each of the movable portions.

9. The medical device of claim 6, wherein each branch member further includes an uncoiled portion between the proximal coil and the sheath.

10. The medical device of claim 6, wherein each of the plurality of proximal coils is directly coupled to the sheath.

11. The medical device of claim 1, wherein each movable portion includes a bridge portion extending distally from a respective distal coil toward an adjacent branch member, wherein, when the basket is in the expanded configuration, the medical device includes a plurality of bridge portions that at least partially define a distally-facing opening, the distally-facing opening being the only distally-facing opening of the basket.

12. The medical device of claim 1, wherein the proximal coil and the distal coil of a given branch member are formed from the same filament.

13. The medical device of claim 12, wherein the uncoiled portion of the given branch member is formed from the same filament as the proximal coil and the distal coil of the given branch member.

14. The medical device of claim 1, wherein the medical device includes a plurality of side openings, wherein each of the plurality of side openings is partially defined by adjacent branch members, and only one side opening is disposed between a given pair of adjacent branch members.

15. A medical device, comprising:
a plurality of branch members forming a basket movable between a collapsed configuration and an expanded configuration, each branch member having:
a proximal coil;
a distal coil;
an uncoiled portion disposed between the proximal coil and the distal coil; and
a movable portion;
wherein each movable portion includes a bridge portion extending distally from a respective distal coil toward an adjacent branch member, and each bridge portion has a shorter length in the collapsed configuration than in the expanded configuration.

16. A medical device, comprising:
a plurality of branch members forming a basket movable between a collapsed configuration and an expanded configuration, each branch member having a proximal coil formed from a filament, a distal coil formed from the same filament as the proximal coil, an uncoiled portion disposed between the proximal coil and the distal coil, and a movable portion, wherein:
each of the plurality of distal coils is staggered about a longitudinal axis of the medical device from a remaining plurality of distal coils; and
each of the plurality of proximal coils is staggered about the longitudinal axis of the medical device from a remaining plurality of proximal coils.

17. The medical device of claim 16, wherein each uncoiled portion is located at approximately a midpoint between a respective distal coil and proximal coil.

18. The medical device of claim 16, wherein the plurality of branch members are formed by an equal number of filaments.

19. The medical device of claim 16, wherein the uncoiled portion of a given branch member is formed from the same filament as the proximal coil and the distal coil of the given branch member.

* * * * *